United States Patent [19]
Rueb et al.

[11] Patent Number: 5,324,843
[45] Date of Patent: Jun. 28, 1994

[54] PROCESS FOR MAKING 3,4,5,6-TETRAHYDROPHTHALIMIDE DERIVATIVES

[75] Inventors: Lothar Rueb, Speyer; Karl Eicken, Wachenheim; Bernd Schaefer, Dierbach; Gernot Reissenweber, Boehl-Iggelheim; Peter Schaefer, Bad Duerkheim, all of Fed. Rep. of Germany

[73] Assignee: BASF Aktiengesellschaft, Ludwigshafen, Fed. Rep. of Germany

[21] Appl. No.: 39,497
[22] PCT Filed: Nov. 16, 1991
[86] PCT No.: PCT/EP91/02166
§ 371 Date: Apr. 29, 1993
§ 102(e) Date: Apr. 29, 1993
[87] PCT Pub. No.: WO92/09575
PCT Pub. Date: Jun. 11, 1992

[30] Foreign Application Priority Data
Nov. 28, 1990 [DE] Fed. Rep. of Germany ....... 4037840

[51] Int. Cl.$^5$ ............................. C07D 209/48
[52] U.S. Cl. ........................ 548/452; 562/20
[58] Field of Search ............. 548/452; 562/20

[56] References Cited
U.S. PATENT DOCUMENTS
4,933,001 6/1990 Plath et al. ............... 71/95
4,959,098 9/1990 Schwalge et al. ......... 71/95

FOREIGN PATENT DOCUMENTS
2008988 8/1990 Canada .
240659 2/1987 European Pat. Off. .

Primary Examiner—David B. Springer
Attorney, Agent, or Firm—Keil & Weinkauf

[57] ABSTRACT 3-(3,4,5,6-tetrahydrophthalimido)cinnamic esters I

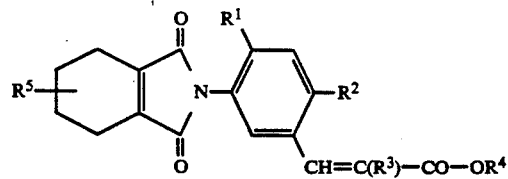

($R^1$=H, halogen; $R^2$, $R^3$=halogen; $R^4$=C-organic radical, $R^5$=H, $CH_3$) are prepared by reducing 3-nitrocinnamic esters II

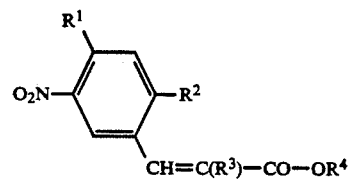

with hydrogen in the presence of a catalyst and condensing the resulting 3-aminocinnamic esters III

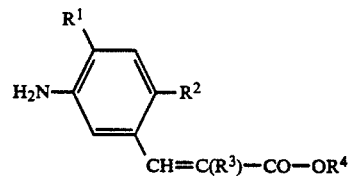

with a 3,4,5,6-tetrahydrophthalic anhydride IV

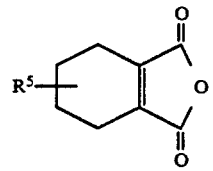

and are valuable active ingredients in crop protection.

4 Claims, No Drawings

PROCESS FOR MAKING 3,4,5,6-TETRAHYDROPHTHALIMIDE DERIVATIVES

The present invention relates to an improved process for preparing 3-(3,4,5,6-tetrahydrophthalimido)cinnamic esters of the formula I

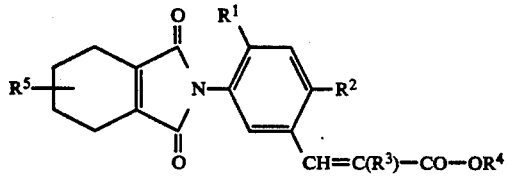

where $R^1$ is hydrogen or halogen, $R^2$ and $R^3$ are halogen, $R^4$ is a C-organic radical of 1 to 6 carbon atoms and $R^5$ is hydrogen or methyl.

It is generally known that nitrocinnamic esters which, however, have no alpha halogen are reduced by iron in acetic acid (JP-A 155 358/84) or hydrogen on a palladium, platinum or Raney nickel catalyst (EP-A 345 637 and DE-A 39 31 615) to aminocinnamic esters and these are converted into tetrahydrophthalimidocinnamic esters of the type of compounds I.

However, according to Bull. Chem. Soc. Jap. 49, (1976) 2284, BE-A 855-464 and EP-A 240 659, when hydrogen is used as reducing agent there is also hydrogenation of the unsaturated side chain of an aromatic compound. EP-A 240 659 also discloses that this side reaction does not occur when platinum oxide is used as catalyst or when metals such as iron are used as reducing agents.

In addition, EP-A 369 212 and Chimia 41, (1987) 73 disclose that catalytic dehalogenation is possible with hydrogen in the presence of catalysts such as palladium, platinum and Raney nickel, and this is in fact used for preparative syntheses in these publications.

It is therefore proposed, to avoid the said competing reactions, in the earlier German Application DE-A 39 31 615 that specifically the 3-nitrocinnamic esters II which have alpha chlorine or bromine be reduced only with mild reducing agents such as tin(II) salts or with iron to the 3-amino esters III.

However, the disadvantage of this method is the problem on the industrial scale of removing and disposing of the tin and iron salts which are the byproducts of the reduction.

It is an object of the present invention to provide better access to the compounds I.

We have found that this object is achieved by a process for preparing 3-(3,4,5,6-tetrahydrophthalimido)cinnamic esters of the formula I, which comprises reducing a 3-nitrocinnamic ester of the formula II

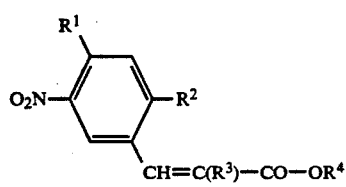

with hydrogen in the presence of a catalyst, and condensing the resulting 3-aminocinnamic ester of the formula III

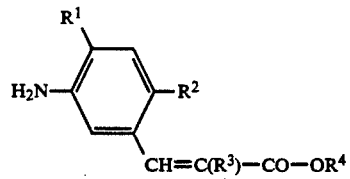

subsequently or simultaneously with a 3,4,5,6-tetrahydrophthalic anhydride of the formula IV

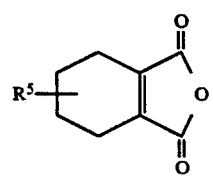

We have also found novel 3-nitrocinnamic esters of the formula II'

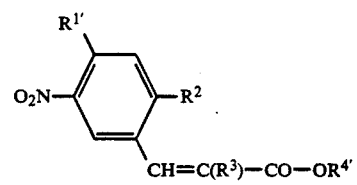

where $R^{1'}$ is hydrogen or fluorine, $R^2$ and $R^3$ are halogen and $R^{4'}$ is $C_1$-$C_4$-alkyl, and novel 3-aminocinnamic esters of the formula III'

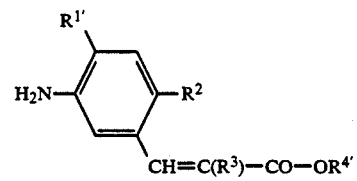

as intermediate.

The 3-nitrocinnamic esters II used as starting materials can be prepared in a variety of ways, preferably by one of the following methods:

(a) reaction of m-nitro aldehydes IV with phosphorus ylides V

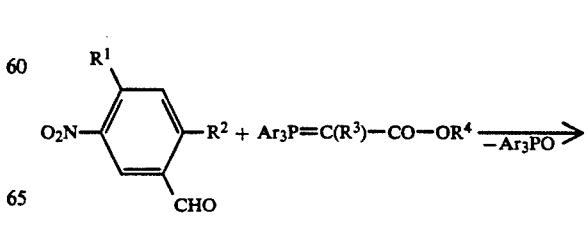

-continued

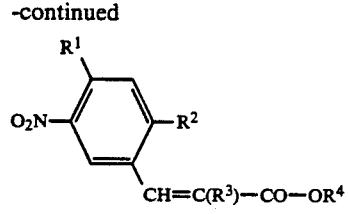

II

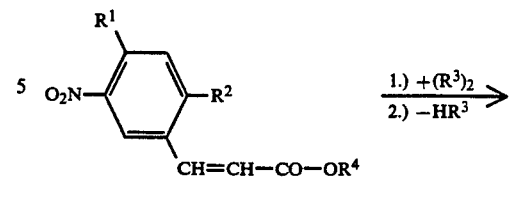

VII

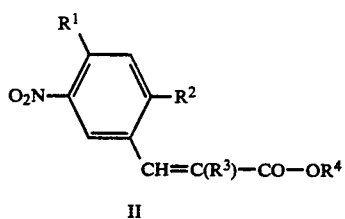

II

The Ar radicals can be identical or different and are C-organic radicals, in particular, phenyl.

The reaction is generally carried out by conventional methods (cf. EP-A 345 637) in an inert solvent or diluent, e.g. alcohols, preferably in $R^4$—OH, or in chlorohydrocarbons such as dichloromethane.

All the starting compounds are preferably employed in approximately the stoichiometric ratio, but an excess of one component, of up to 10 mol %, may be advisable in some cases.

The reaction is normally carried out at from 0° C. to the boiling point of the solvent.

No special conditions relating to the pressure are necessary; the reaction is therefore expediently carried out under atmospheric pressure.

The starting compounds IV are known. The phosphorus ylides V can be prepared by conventional methods [e.g. Chem. Ber. 95, (1962) 3003].

(b) Nitration of cinnamic esters VI

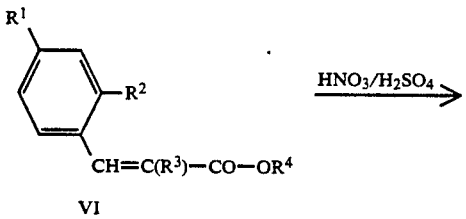

The reaction is carried out by conventional methods (cf. also JP-A 155 358/84), if required in an inert solvent or diluent at from −10° to 50° C.

The amount of nitration reagent is not critical. It is preferable to use an excess of nitration reagent in sulfuric acid or without solvent in nitric acid.

The statements concerning the pressure made for method (a) apply. The preparation of the starting compounds can be similar to method (a).

(c) Halogenation of m-nitrocinnamic esters VII

The reaction is generally carried out in a conventional manner (cf. EP-A 240 659) in an inert solvent or diluent, e.g. a halohydrocarbon such as methylene chloride, chloroform, tetrachloromethane, 1,1,1-trichloroethane and chlorobenzene.

An excess of halogen $(R^3)_2$ of up to about 10 mol % based on the amount of VI is preferably employed.

The reaction is normally carried out at from 0° C. to the boiling point of the solvent, in particular from 15° to 40° C.

Once again, atmospheric pressure is advisable.

In the case of the chlorination of the m-nitrocinnamic esters VII, a particularly advantageous embodiment of method (c) comprises chlorinating the m-nitrocinnamic ester VII in the presence of a Lewis acid and subjecting the resulting α,β-dichloro-β-(2-nitrophenyl)propionic ester (as mixture of diastereoisomers) to elimination of hydrogen chloride.

Particularly suitable Lewis acids are transition metal halides such as zinc(II) chloride, iron(III) chloride and aluminum chloride.

Suitable and preferred solvents are chlorohydrocarbons such as dichloromethane and 1,2-dichlorobenzene.

The amount of Lewis acid is not critical; in general from 2 to 200 mol %, preferably 5 to 140 mol %, of Lewis acid, based on the amount of m-nitrocinnamic ester VII, are used.

To avoid long reaction times, it is advisable to carry out the reaction at from 20° C. to the boiling point of the reaction mixture, in particular from 50° to 90° C.

The subsequent elimination of hydrogen chloride takes place in the presence of an auxiliary base, preferably without introducing or dissipating energy.

The stereochemistry of the elimination can be controlled by the choice of the base, so that the E or Z isomer of the 3-nitrocinnamic esters II is predominantly obtained.

Examples of suitable auxiliary bases are the alkaline earth metal salts of organic acids or organic amines. Very particularly preferably used is sodium acetate in glacial acetic acid, or triethylamine in methylene chloride, in which case the Z isomer of the 3-nitrocinnamic esters II is the main product.

The α,β-dichloro-β-(2-nitrophenyl)propionicester and the base are preferably employed in the stoichiometric ratio, or a small excess of base of up to about 10 mol % is used.

The starting compounds VII can be obtained in a similar manner to method (a) or (b).

(d) Reaction of nitrocinnamoyl chlorides VIII with alcohols IX

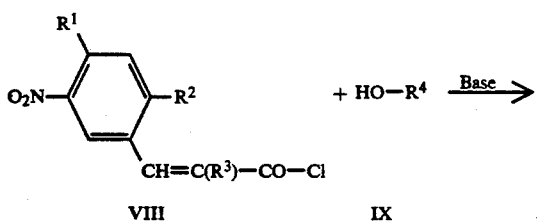

VIII    IX

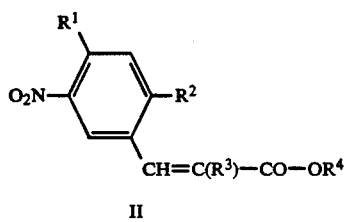

II

The reaction is generally carried out in a conventional manner (cf. Houben-Weyl, Methoden der Organischen Chemie, Volume X/2, 747) in an inert solvent or diluent, advantageously in the presence of a base.

Suitable solvents or diluents are, in particular, fairly high-boiling hydrocarbons such as o-, m-or p-xylene and toluene, esters such as ethyl acetate, and ethers such as dioxane and tetrahydrofuran.

Suitable and preferred bases are tertiary amines such as triethylamine and pyridine, and inorganic salts, e.g. alkali metal hydroxides such as sodium and potassium hydroxide and alkali metal carbonates such as sodium carbonate.

The reaction is normally carried out at from $-10°$ to 200° C., in particular from 0° to 150° C.

The statements concerning the ratios of amounts and the pressure made for method (a) apply.

The cinnamoyl chlorides VIII can be obtained by conventional methods (cf. EP-A 240 659, Example 8).

The nitrocinnamic acid derivatives II are reduced according to the invention using hydrogen in the presence of a metal catalyst, e.g. palladium, platinum and nickel, to the corresponding aminocinnamic acid derivatives II.

The reduction is expediently carried out in an inert polar solvent or diluent, for example an ether such as tetrahydrofuran, an amide such as dimethylformamide, a short-chain carboxylic acid such as acetic or propionic acid, an ester of a short-chain carboxylic acid such as ethyl acetate, or the alcohol HO—$R^4$, especially in methanol or ethanol.

The amount of catalyst is not critical; normally, 1 to 50 mol % of catalyst based on the amount of nitrocinnamic acid derivative II is used.

The hydrogenation is expediently carried out under a pressure of from 1 to 100 bar, preferably from 1 to 10 bar, with hydrogen.

The reaction is generally carried out at from 0° C. to the boiling point of the solvent.

The process can be carried out either batchwise or continuously. When carried out continuously, the nitrocinnamic acid derivative in a solution saturated with hydrogen is preferably passed over a fixed bed which has been coated with the catalyst.

In a preferred embodiment, hydrogen is metered into a mixture of nitrocinnamic acid derivative II, diluent and catalyst until no further consumption of hydrogen is detectable.

The mixture is worked up in a conventional manner so that details on this are unnecessary.

The resulting 3-aminocinnamic acid derivatives III are subsequently converted by condensation with 3,4,5,6-tetrahydrophthalic anhydrides of the formula IV into the 3-(3,4,5,6-tetrahydrophthalimido)cinnamic esters I:

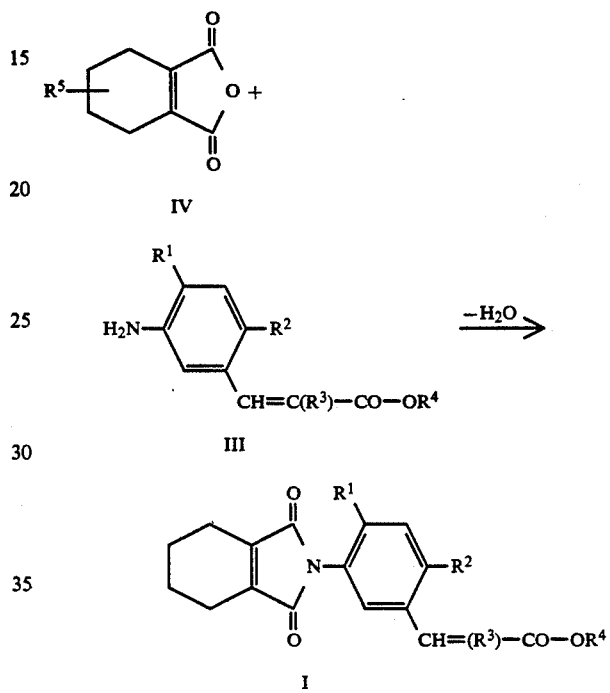

The reaction is normally carried out in an inert aprotic solvent at from 20° C. to the boiling point of the solvent, in particular from 40° to 140° C.

Suitable solvents are lower alkanoic acids such as glacial acetic acid, propionic acid and isobutyric acid, the esters of the said acids such as ethyl acetate, aromatic hydrocarbons such as toluene and o-, m- and p-xylene, and aprotic solvents such as dimethyl- and diethylformamide. When an aprotic solvent is used, continuous removal of the water which is produced is advisable.

The starting compounds III and IV are expediently employed in the stoichiometric ratio, but an excess of one of the components, of up to about 10 mol %, may be advisable in some cases.

The reaction is preferably carried out under atmospheric pressure or the autogenous pressure of the solvent. Lower or higher pressure is possible but generally has no advantages.

A particularly advantageous variant of the process according to the invention comprises the products III which have been obtained by reduction of the 3-nitrocinnamic acid derivatives II being reacted with the 3,4,5,6-tetrahydrophthalic anhydrides IV without isolation from the reaction mixture. It is possible in this procedure for the 3,4,5,6-tetrahydrophthalic anhydride IV to be introduced into the reaction mixture before or after the hydrogenation. In this case, the reaction is preferably carried out in a lower alkanoic acid, especially in propionic acid, or in an aprotic solvent, especially in an ether such as tetrahydrofuran or an amide such as dimethylformamide.

The process according to the invention can be used successfully to synthesize all 3-(3,4,5,6-tetrahydrophthalimido)cinnamic acid derivatives I as defined with α-chlorine or bromine, particularly those compounds in which the substituents have the following meanings:

$R^1$—hydrogen or halogen such as fluorine, chlorine, bromine and iodine, especially hydrogen or fluorine;
$R^2$—halogen as mentioned above, especially chlorine;
$R^3$13 chlorine or bromine;
$R^4$13 hydrogen;
— $C_1$-$C_4$-alkyl such as methyl, ethyl, n-propyl, isopropyl, n-butyl and tert-butyl, and the alkyl can also carry one or two $C_1$-$C_4$-alkoxy radicals such as methoxy, ethoxy, n-propoxy, isopropoxy, n-butoxy and tert-butoxy, especially methoxy and ethoxy, and/or $C_1$-$C_4$-alkylthio radicals such as methylthio, ethylthio, n-propylthio, isopropylthio, n-butylthio and tert-butylthio, especially methylthio;
— $C_3$-$C_7$-cycloalkyl such as cyclopropyl, cyclobutyl, cyclopentyl and cyclohexyl;
— $C_3$-$C_6$-alkenyl such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl,1,1-dimethyl-2-butenyl,1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl;
— $C_3$14 $C_6$-alkynyl such as 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;
—benzyl;
$R^5$ hydrogen or methyl.

The 3-nitrocinnamic acid derivatives II' and the 3-aminocinnamic acid derivatives III' where $R^{1'}$ is hydrogen or fluorine, $R^2$ and $R^3$ are halogen and $R^{4'}$ is $C_1$-$C_4$-alkyl as mentioned above are novel. Particularly preferred derivatives II' and III' are those where $R^2$ is chlorine and $R^3$ is chlorine or bromine.

3-(3,4,5,6-Tetrahydrophthalimido)cinnamic esters I are used in crop protection, especially as herbicides (preferably in cereals) and as abscission agents (in cotton).

PREPARATION EXAMPLES (E/Z)-N-[3-(2-chloro-2-ethoxycarbonylvinyl)-4-chlorophenyl]-3,4,5,6-tetrahydrophthalimide

EXAMPLE 1

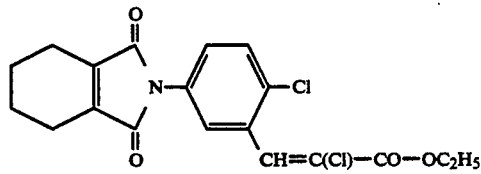

EXAMPLE 1

456 g (3 mol) of 3,4,5,6-tetrahydrophthalic anhydride were added a little at a time to a solution of 780 g (3 mol) of ethyl (E/Z)-2,alpha-dichloro-5-aminocinnamate in 7 l of propionic acid at 20° to 25° C. The resulting clear solution was stirred at 60° C. for 5 hours, during which the product started to crystallize. The mixture was cooled to about 25° C. and diluted with 4 l of water and then stirred for at least 14 hours. The product was then separated off, washed with 4.5 l of water and dried.

Yield: 80% (purity about 98% by HPLC); melting point: 111°–112° C.

Precursor 1α

Ethyl (E/Z)-2,alpha-dichloro-5-nitrocinnamate

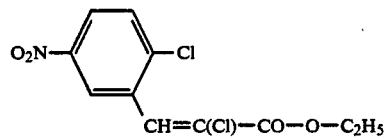

by method (a):

84.1 g (0.22 mol) of ethoxycarbonyl(chloro)methylenetriphenylphosphorane were added to a solution of 37 g (0.2 mol) of 2-chloro-5-nitrobenzaldehyde in 350 ml of ethanol. The mixture was stirred at 25° C. for one hour, after which the product was filtered off and washed with petroleum ether.

Yield: 70%; melting point 97°–98° C.

by method (c):

0.64 g (4 mmol) of anhydrous iron(III) chloride was added to a solution of 10 g (39 mmol) of ethyl 2-chloro-5-nitrocinnamate in 150 ml of 1,2-dichlorobenzene, after which chlorine was passed in at 100° C. for 3 hours. The reaction mixture was subsequently washed with saturated sodium bicarbonate solution and with water, dried over sodium sulfate and concentrated. Yield: 75% of ethyl α,β-dichloro-β-(2-chloro-5-nitrophenyl)propionate (3:1 diastereomer mixture); melting point 63°–65° C.

1 g (3 mmol) of the ethyl α,β-dichloro-β- (2-chloro-5-nitrophenyl)propionate obtained above was dissolved in 30 ml of methylene chloride, after which 0.31 g (3 mmol) of triethylamine was added to the solution. The mixture was stirred at 20°-25° C. for about 15 hours, then washed twice with water, dried with sodium sulfate and concentrated under reduced pressure.

Yield: 100% of a crude product which still contained 5 to 10% of the dichloro compound.

Precursor 1β

Ethyl (E/Z)-2,alpha-dichloro-5-aminocinnamate

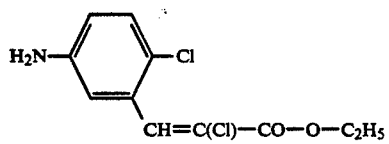

3 g (51 mmol) of Raney nickel were added to a suspension of 5.8 g (20 mmol) of ethyl (E/Z)-2,alpha-dichloro-5-nitrocinnamate in 150 ml of ethanol. After injection of 1.05 bar of hydrogen, the mixture was stirred at 30° C. until hydrogen uptake ceased (about 7 hours). The catalyst was then separated off, the solvent was removed and the residue was washed with petroleum ether.

Yield: 77%; melting point 110°–111° C.

EXAMPLE 2 (ONE-STAGE VARIANT)

A mixture of 29 g (100 mmol) of ethyl 2,alpha-dichloro-5-nitrocinnamate, 3 g (51 mmol) of Raney nickel, 15.2 g (100 mmol) of 3,4,5,6-tetrahydrophthalic anhydride and 100 ml of propionic acid was hydrogenated at 50° to 60° C. by injection of 1.05 bar of hydrogen until hydrogen uptake ceased (about 18 hours). The catalyst was then removed from the still hot reaction mixture, and 100 ml of water were added to the resulting solution. After stirring for 30 minutes, the crystallized product was separated off and washed with water until neutral.

Yield: 85%; melting point 108°–110° C.

We claim:

1. A process for preparing a 3-(3,4,5,6-tetrahydrophthalimido)cinnamic ester of the formula I

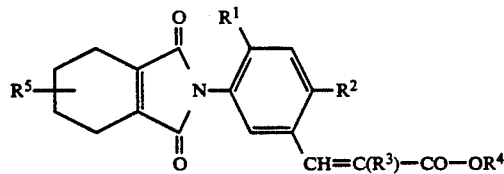

where $R^1$ is hydrogen or halogen, $R^2$ and $R^3$ are halogen, $R^4$ is hydrogen, $C_1$–$C_4$-alkyl, $C_3$–$C_7$-cycloalkyl, $C_3$–$C_6$-alkenyl, $C_3$–$C_6$-alkynyl or benzyl and $R^5$ is hydrogen or methyl, which comprises reducing a 3-nitrocinnamic ester of the formula II

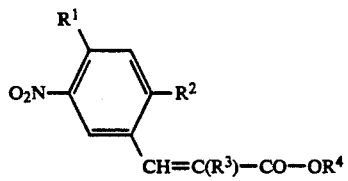

with hydrogen in the presence of a catalyst, and condensing the resulting 3-aminocinnamic ester of the formula III

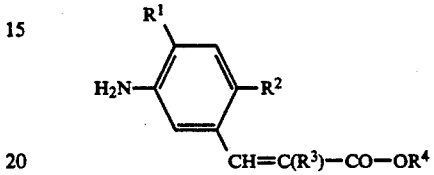

subsequently or simultaneously with a 3,4,5,6-tetrahydrophthalic anhydride of the formula IV

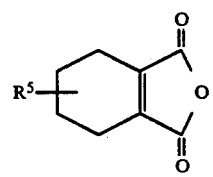

2. The process of substituted claim 1, wherein the reduction is carried out in a polar solvent.

3. The process as claimed in claim 1, which starts from a 3-nitrocinnamic ester II as produced in the preparation of II by halogenation of an m-nitrocinnamic ester of the formula VII

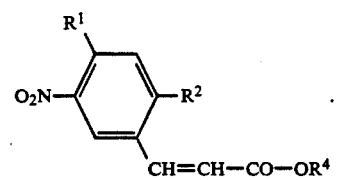

4. The process as claimed in claim 1, which starts from a 3-nitrocinnamic ester II as produced in the reaction of an m-nitro aldehyde IV

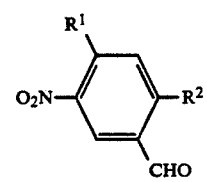
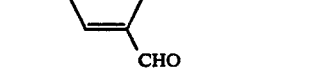

with a phosphorus ylide V

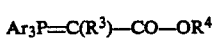

* * * * *

UNITED STATES PATENT AND TRADEMARK OFFICE
CERTIFICATE OF CORRECTION

PATENT NO.: 5,324,843

DATED: June 28, 1994

INVENTOR(S): RUEB et al.

It is certified that error appears in the above-identified patent and that said Letters Patent is hereby corrected as shown below:

Column 10, claim 2, line 33, delete "substituted".

Signed and Sealed this

Eighth Day of November, 1994

Attest:

BRUCE LEHMAN

Attesting Officer

Commissioner of Patents and Trademarks